(12) United States Patent
Asami et al.

(10) Patent No.: US 6,430,477 B1
(45) Date of Patent: Aug. 6, 2002

(54) CONTROL APPARATUS FOR GAS ANALYZER SYSTEM AND CONTROL METHOD THEREOF

(75) Inventors: Tetsuji Asami; Akihiro Nishimoto, both of Miyanohigashi-machi (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/107,705

(22) Filed: Jun. 30, 1998

(30) Foreign Application Priority Data

Jul. 12, 1997 (JP) .............................................. 9-202359

(51) Int. Cl.[7] .............................................. G01M 1/38
(52) U.S. Cl. ....................................... 700/266; 700/278
(58) Field of Search ........................... 702/24; 700/266, 700/3, 9, 10; 73/23.2

(56) References Cited

U.S. PATENT DOCUMENTS

| | | | |
|---|---|---|---|
| 4,638,443 A | * | 1/1987 | Kaneyasu et al. ........... 364/497 |
| 5,055,260 A | * | 10/1991 | Roberge et al. ............... 422/62 |
| 5,265,031 A | * | 11/1993 | Malczeewski .............. 364/497 |
| 5,304,797 A | * | 4/1994 | Irie et al. ..................... 250/280 |
| 5,550,752 A | * | 8/1996 | Federspiel .................. 364/505 |
| 5,659,125 A | * | 8/1997 | Ernst .......................... 73/1.03 |
| 5,764,150 A | * | 6/1998 | Fleury et al. ............... 340/632 |
| 5,895,432 A | * | 4/1999 | Zarchy .......................... 701/2 |

FOREIGN PATENT DOCUMENTS

| | | |
|---|---|---|
| GB | 2 284 059 A | 5/1995 |
| JP | 08 159 968 | 6/1996 |

OTHER PUBLICATIONS

Gay S, "Modular, Digital, Gas Analyzer Architecture Re–thinking The Approach To Analytical Measurements", Advances in Instrumentation and Control, US, Instrument Society of America, Research Triangle Park, vol. 49, No. Part 02, 1994, pp. 197–208, XP000491427 ISSN: 1054–0032.

Adani et al, "Using Predictive Maintenance in The Next Generation Of On–Line Gas Analyzers", Advances in Instrumentation and Control, US, Instrument Society of America, Research Triangle Park, vol. 50, No. Part 02, Oct. 1, 1995 pp. 281–287 XP000540644 ISSN: 1054–0032.

Harvey I et al, "The Development of An Environmental Chamber For The Characterization Of Gas Sensors", Sensors and Acutators, CH, Elsevier Sequoia S.A. Lausanne, vol. 16, No. 4, Apr. 1, 1989 pp. 393–405, XP000140570.

* cited by examiner

Primary Examiner—Bipin Shalwala
Assistant Examiner—Nitin Patel
(74) Attorney, Agent, or Firm—Oppenheimer Wolff & Donnelly LLP

(57) ABSTRACT

A control apparatus for a gas analyzer system for controlling a plurality of analyzers having different hardware constitutions in a single program works on a single CPU. The control apparatus includes a processing unit with a CPU which is connected with each gas analyzer by a CPU bus to control each gas analyzer. Each gas analyzer is provided with a plurality of AD converters having respectively a plurality of analog input ports in which the respective output signals of the gas analyzer units are inputted, and a non-volatile memory unit for storing a connection condition table which shows the connection condition of the gas analyzer unit to the AD converters, by connecting with the CPU bus, thereby making it possible for the CPU in the analyzer processing unit to control the respective gas analyzers by a single program.

11 Claims, 2 Drawing Sheets

CONTROL APPARATUS FOR GAS ANALYZER SYSTEM AND CONTROL METHOD THEREOF

FIELD OF THE INVENTION

The present invention relates to a control apparatus for a gas analyzer system applicable, for example, to an automobile exhaust gas analyzer and a control method thereof.

DESCRIPTION OF THE PRIOR ART

In general, a gas analyzer system such as an automobile exhaust gas analyzer is required to be composed of a plurality of gas analyzers to measure various kinds of gases such as CO, $CO_2$, THC, and $NO_x$. The gas analyzers include a nondispersive infrared analyzer (hereinafter to be referred to as NDIR), a flame ionization detector (hereinafter to be referred to as FID), chemi-luminescent detector (hereinafter to be referred to as CLD), etc. Thus, multi-component gases to be measured such as automobile exhaust gas have so far been analyzed by a gas analyzer system comprising a plurality of gas analyzers for analyzing the specific gases and the gas analyzer processors connected to those gas analyzers.

FIG. 2 is a block diagram to show the control apparatus for the conventional gas analyzer system 20. In FIG. 2, the gas analyzer system 20 comprises an analyzer processor 21, analyzers 22–24 for analyzing respectively different specified gases, and cables 25 for connecting the respective parts 21–24.

The analyzers 22–24 respectively have analyzer substrates 26–28 and analyzers 30–32, and the respective analyzer substrates 26–28 are provided with CPUs 26a–28a and non-volatile memories in which the programs for operating the CPUs 26a–28a are written (hereinafter to be referred to as ROM) 26b–28b. In other words, in this gas analyzer system 20, due to the provision of the CPUs 26a–28a on the respective analyzers 22–24, individual controls of the analyzers 30=32 are made by these CPUs 26a–28a. By mediating the inputted measuring signals through the communication part 29 and the cables 25, the signals are transmitted to the analyzer processor 21.

On the other hand, the analyzer processor 21 is provided with the CPU 21a and the ROM 21b, in which the program for operating the CPU 21a is written, so that it is possible to calculate the concentration value of various kinds of gases by processing the measuring signals inputted through the communication part 29, and to display the results on the screen 21d or the like by outputting the results to the display processor 21c or the like.

Because the constitutions of the respective analyzers 30–32 are respectively different, the above analyzer substrates 26–28 are provided with the AD converters 26c–26g, 27c, 27d, 28c–28f for inputting the analog signals outputted from various gas analyzers A of the respective analyzers 30–32 and sensors S. The AD converters 26c, 26d, 27c, 28c, 28d are each an AD converter having one analog input port, making it possible to input the analyzing results from the gas analyzer A at a high speed. On the other hand, the AD converters 26f, 26g, 27d, 28e each has a multiplexer for changing over the four analog input ports, to which the measured values are inputted at a relatively low speed from the sensors for determining the sample flow amount, change in source voltage, temperature, etc. In the AD converter 26e or 28c which is provided with two or three analog input ports, the measured values are inputted at an intermediate speed.

Furthermore, the AD converters 26c–26g, 27c, 27d, 28c–28f self-contain respectively an amplifier for gain adjustment, being so constituted as to convert the measured values inputted from the analyzers 30–32 appropriately to digital signals.

Accordingly, the CPUs 26a–28a are to carry out individually the gain adjustments of these AD converters 26c–26g, 27c, 27d, 28c–28f and control of the input speed of the measured values in conformity with the number and characteristics of the gas analyzers A and various sensors S in the analyzer units 30–32.

The gas analyzer system 20 as described above controls the analyzer units 30–32 in the unit of the analyzers 22–24, so that it describes the hardware information inherent to the analyzers 22–24 as the programs for the individual CPUs 26a–28a. Accordingly, it has been necessary to compose programs for the individual analyzers 22–24 to give different operation commands to the respective CPUs 26a–28a, write these programs in the ROMs 26b–28b, and set them to the analyzer substrates 26–28. For this purpose, when a new type of apparatus having the analyzer units 30–32 having different number of sensors and performance is manufactured, the number and performance of the AD converter are required to be changed, for which it becomes necessary to redesign the whole analyzer substrates 26–28 or newly recompose the program for the CPUs 26a–28a, requiring a great deal of time and labor.

Above all, in the case of making a version of the gas analyzer system 20 which is already in use by the customers, when a change has been made in the number of the input signals from the analyzer unit or characteristics due to the improvement of the analyzer units 30–32, it requires time for the work of rewriting the programs written on the ROMs 26b–28b, and the version-up work is laborious.

In view of the above, it can be considered to make programming in a manner to make direct control of the analyzers 30–32 and AD converters 26c–26g, 27c, 27d, 28c–28f in CPU 21a in the analysis processing unit 21 and to write the program in the ROM 21b. However, when there are provided plural programs for controlling plural analyzers 22–24 in one CPU 21a, inversely it becomes necessary to modify the whole program for the sole purpose of changing the control method of one analyzer. In addition, because the control programs for the analyzers 30–32 include many common portions, to change only a part of the programs for making the similar processings tends to induce the generation of erroneous programming, leading to a danger of changing the control programs of other analyzers which need not be changed, thus making the controls more complicated.

SUMMARY OF THE INVENTION

The present invention has been made in consideration of the matters described above. Its objects, are to provide a control apparatus for the gas analyzer system for controlling a plurality of analyzers having different hardware constitutions in a single program which works on a single CPU, and a method for its control.

To attain the above objects, the control apparatus for the gas analyzer system of the present invention is characterized in that, in a gas analyzer system comprising a plurality of gas analyzers having gas analyzer units for analyzing respectively specified gases and an analyzer processing unit connected to these gas analyzers, the analyzer processing unit is provided with a CPU which is connected with each gas analyzer by a CPU bus and designed to control each gas analyzer. Each gas analyzer is provided with a plurality of AD converters having respectively a plurality of analog input ports in which the respective output signals of the gas analyzer units are inputted, and a non-volatile memory unit for storing the connection condition table which shows the connection condition of the gas analyzer unit to these AD converters. By connecting to the CPU bus, the CPU in the analyzer processing unit can control the respective gas analyzers by a single program.

The control method of the gas analyzer system of the present invention is characterized in that, in a gas analyzer system comprising a plurality of gas analyzers having gas analyzer units for analyzing respectively specified gases and an analyzer processing unit connected to these gas analyzers, and being provided with a plurality of AD converters having respectively plural analog input ports in each gas analyzer and a non-volatile memory unit irrespective of the kind of the gas analyzer, a table of connection conditions to show the input condition of the output signals of the gas analyzer unit to the analog input port of each AD converter is stored in the memory unit. The signal which is inputted to the AD converter in each gas analyzer above is read out by the CPU in the analyzer processing unit while referring to the connection condition table stored in the memory unit, thereby reading out the analog input from the gas analyzer unit which outputs respectively different signals by a single program irrespective of the kind of the gas analyzer to control each gas analyzer.

Accordingly, by referring to the above connection condition table, the CPU in the analyzer processing unit can regard the different analyzers in the analyzer means (gas analyzer unit) to be identical. In other words, because of the fact that the plural analyzers can be appropriately controlled using a single program working on a single CPU, even in case the gas analyzer system covers diversified kinds of analyzers such as NDIR, FID, CLD, etc., control can be made by a single program, and simplification can be obtained.

Further, in each gas analyzer, because the hardware information inherent to the analyzer is controlled in the form of a table, even in case of upgrading of the gas analyzer unit, the system can be coordinated simply by writing the table of connection condition coordinates with the new gas analyzer unit in the memory unit or replacing with the memory unit in which the above connection condition table is written. In other words, because the system operation can be met simply by alteration of the connection condition table even in case of the change of the hardware of gas analyzer, there is no necessity to rewrite the program to the CPU in the analyzer processing unit.

Furthermore, as there is no necessity to load a CPU in the unit of the gas analyzer, the constitution of the analyzer substrate of each gas analyzer can be simplified. In addition, by sufficiently providing the number of the AD converters, the analyzer substrates in the gas analyzers can be commonly designed utterly irrespective of the kind of the gas analyzer unit, so that the labor required for the designing can be suppressed as far as possible.

The above connection condition table may be so designed as to have an AD converter changeover table which, when the CPU reads out the signal from each gas analyzer in the unit time, records the plural numbers of the AD converter changeover information carrying the input port number of the AD converter to be read out and the channel number assigned to the input port by the number of the AD converters, and provides one of the plural kinds of AD converter changeover information sequentially per unit time.

In this case, the CPU may appropriately change over the input port of the AD converter to meet the connection condition with the gas analyzer unit so as to make it possible to read out the required measuring signal and regulate the reading speed of each measuring signal inputted from the gas analyzer unit.

The above connection condition table may have the channel information table which has records of the channel specific information of the number of channels containing the channel specific information having respective channel numbers, numerical amount which shows the magnitude for gain adjusting the analog signal inputted to the channel in an AD converter, a flag to show if the spike noise is included in the analog signal, a flag to show whether it is necessary to make gain correction on the CPU side or not, and the numerical value showing the measuring space.

In this case, the CPU can appropriately process the measuring signal of each channel inputted from the gas analyzer unit and calculate the concentration of the measured gas, and also optionally control the AD converter in tune with the analog measuring signal inputted to each channel.

The connection condition table written in the memory unit as described above shows the minimum necessary information for indicating the connection condition of the hardware inherent to the respective analyzer, and correspondence of the connection condition table to the hardware connection condition is easy to understand. Accordingly, in comparison with the individual setting of the program conforming to the hardware of each gas analyzer unit, the information amount to be memorized is exceedingly small and the corresponding relations between them are easy to understand. Consequently, it is possible to suppress as much as possible the generation of errors in case of development of a new type of apparatus or upgrade of the system.

DETAILED DESCRIPTION OF THE PREFERRED EMBODIMENTS

Figure 1:
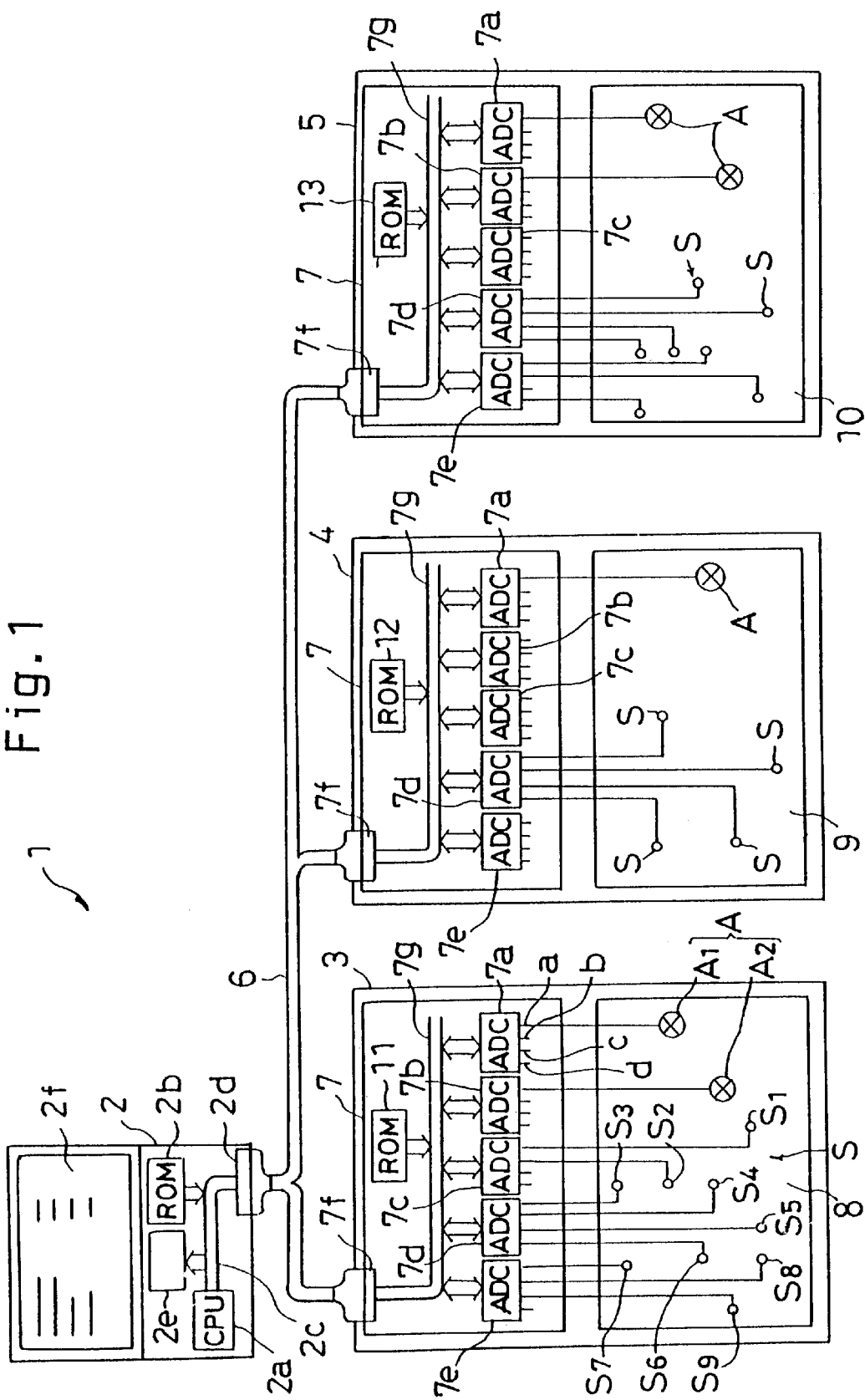
FIG. 1 is a block diagram showing the control apparatus of the gas analyzer system which shows an embodiment of the present invention and FIG. 2 is a block diagram showing an embodiment of a conventional gas analyzer system.
Figure 2:
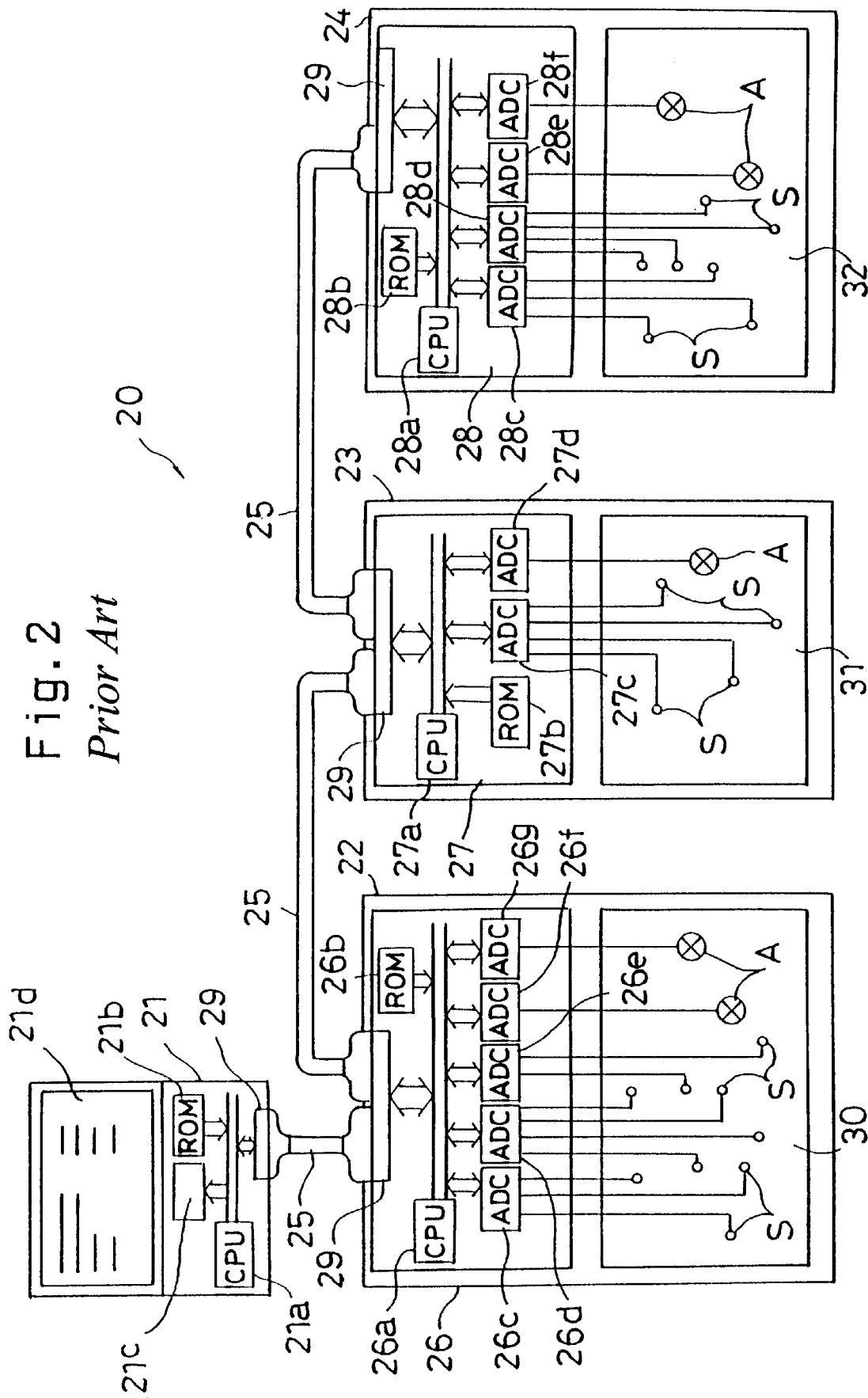

FIG. 1 is a block diagram showing the control apparatus of the gas analyzer system 1 which shows an embodiment of the present invention. In FIG. 1, the gas analyzer system 1 comprises an analyzer processing unit 2, gas analyzers 3–5 for analyzing the respectively different specified gases, and a CPU bus 6 for connecting the elements 2–5.

The gas analyzers 3–5 have analyzer substrates 7 and gas analyzer units 8–10. Each analyzer substrate 7 self-contains a multiplexer, and has, for example, four analog input ports a–d (hereinafter simply referred to as ports), and five AD converters 7a–7e, each of which self-contains an amplifier for input gain adjustment. Non-volatile ROMs 11–13 are connected through a buffer 7f and a CPU bus 7g to the CPU bus 6. Namely, in this gas analyzer system 1, the AD converters 7a–7e of the gas analyzers 3–5 and the ROMs 11–13 which can be electrically rewritten with repetition (hereinafter to be referred to as EEPROM) are connected to the analyzer processing unit 2 through the CPU bus 6.

On the other hand, the analyzer processing unit 2 is provided with a CPU 2a, a memory unit 2b in which the program for operating the CPU 2a is written (hereinafter to be referred to as memory), a CPU buss 2d, and a buffer 2d for connecting the CPU bus 2c to the CPU bus 6, by which the measuring signals from the AD converters 7a–7e read out through the CPU bus 6 are processed to calculate the concentration values of various kinds of gases. The concentration values can be displayed on the screen 2f and the like by outputting to the display processing unit 2e and the like. The buffer 2d, display processing unit 2e, and screen 2f are not indispensable elements of the present invention but may be omitted.

Accordingly, in the case of the above gas analyzer system, although the constitutions of the gas analyzers 8–10 are different from one another, the analyzer substrates 7 loaded on the gas analyzer units 8–10 are of identical constitutions, with the only exception of being the EEPROMs 11–13 stored with the connection condition table which shows the connection conditions of the gas analyzer units 8–10.

Needless to say, the number of the AD converters to be used in the present invention, the performances such as the number of the ports held by each AD converter, existence or not of adjusting amplifier, etc. are not necessarily limited to those described above, but they may be optionally selected to meet the number and characteristics of the existing gas analyzer units 8–10 and the gas analyzers A and various sensors S which are slated to be put to be upgraded in the future.

Next, citing an example of the gas analyzer 3 out of the above gas analyzers 3–5, the contents of the connection condition table to be recorded on the EEPROM 11 will be described. Also, the method for the CPU 2a to control the gas analyzer unit 8 through the AD converters 7a–7e by using the connection condition table will be explained.

The following Table 1 is a table to show the connection conditions of the gas analyzer unit 8 to the respective AD converters 7a–7e. As shown in Table 1, the AD converters 7a, 7b use port a only, to which the outputs of the gas analyzers $A_1$, $A_2$ of FIG. 1 are connected to provide channels 1, 2. For the AD converter 7c, ports a, b are used to which the sensors $S_1$, $S_2$ are connected, respectively, to make channels 3, 4. Similarly, in the AD converter 7d, sensors $S_3$–$S_6$ are connected to ports a–d, which constitute channels 5–8. In the AD converter 7e, sensors $S_7$–$S_9$ are connected to ports a–c, to make the channels 9–11.

TABLE 1

| AD converter | port | channel | connected sensor |
|---|---|---|---|
| 7a | a | CH 1 | gas analyzer $A_1$ |
|  | b |  |  |
|  | c |  |  |
|  | d |  |  |
| 7b | a | CH 2 | gas analyzer $A_2$ |
|  | b |  |  |
|  | c |  |  |
|  | d |  |  |
| 7c | a | CH 3 | sensor $S_1$ |
|  | b | CH 4 | sensor $S_2$ |
|  | c |  |  |
|  | d |  |  |
| 7d | a | CH 5 | sensor $S_3$ |
|  | b | CH 6 | sensor $S_4$ |
|  | c | CH 7 | sensor $S_5$ |
|  | d | CH 8 | sensor $S_6$ |
| 7e | a | CH 9 | sensor $S_7$ |
|  | b | CH 10 | sensor $S_8$ |
|  | c | CH 11 | sensor $S_9$ |
|  | d |  |  |

The above CPU 2a is so programmed as to read out the respective AD converters 7a–7e example, every 25 ms (unit time) in order. In the AD converter changeover table shown in the following table 2, there are shown sequentially eight kinds of AD converter changeover information based on 200 ms as 1 cycle. The above unit time can be optionally selected to meet the operating speed of the system.

TABLE 2

| sampling time | AD Converter 7a | | AD Converter 7b | | AD Converter 7c | | AD Converter 7d | | AD Converter 7e | |
|---|---|---|---|---|---|---|---|---|---|---|
|  | MUX | CH | MUX | CH | MUX | CH | MUX | CH | MUX | CH |
| 25 | 1 | 1 | 1 | 2 | 1 | 3 | 1 | 5 | 1 | 9 |
| 50 | 1 | 1 | 1 | 2 | 2 | 4 | 2 | 6 | 2 | 10 |
| 75 | 1 | 1 | 1 | 2 | 1 | 3 | 3 | 7 | 3 | 11 |
| 100 | 1 | 1 | 1 | 2 | 2 | 4 | 4 | 8 | — | — |
| 125 | 1 | 1 | 1 | 2 | 1 | 3 | 1 | 5 | 1 | 9 |
| 150 | 1 | 1 | 1 | 2 | 2 | 4 | 2 | 6 | 2 | 10 |
| 175 | 1 | 1 | 1 | 2 | 1 | 3 | 3 | 7 | 3 | 11 |
| 200 | 1 | 1 | 1 | 2 | 2 | 4 | 4 | 8 | — | — |

Now, referring to the AD converter changeover information when the sampling time is 25 ms, the amounts to be outputted to the multiplexers (expressed as "MUX" in the table) of the AD converters 7a–7e are all 1. Accordingly, when the sampling time is 25 ms, all AD converters 7a–7e select port a. The signals to be inputted from the respective AD converters 7a–7e represent to be the analog signals of channels 1, 2, 3, 5, and 9 in order.

Next, referring to the AD converter changeover information when the sampling time is 50 ms, the amounts of the AD converters 7a–7e to be outputted to the multiplexers are 1, 1, 2, 2 and 2 in order. Accordingly, at this time, the AD converters 7a, 7b select port a, and AD converters 7c–7e select port b. The signals to be inputted from the AD converters 7a–7e are those of channels 1, 2, 4, 6 and 10 in order.

In the same manner, the CPU 2a repeats the samplings 8 times up to 200 ms and inputs the signals of the respective channels while referring to the AD converter changeover information in order, and after completion of the 1 cycle measurement, it changes over the multiplexers of the AD converters 7a–7e and inputs the signals of the respective channels.

In other words, in the above example, the AD converters 7a, 7b which do not change over the multiplexer port a can input the analog data every 25 ms. This is effective for the case of measuring the signals which vary at high speed. Because of this, in this example, the AD converters 7a, 7b are used for the inputs of the measuring signals from the gas analyzers $A_1$, $A_2$ (ref FIG. 1).

In the case of AD converter 7c which changes over the two ports a, b of the multiplexer, one channel can input the signal every 50 msec. In the case of the AD converters 7d, 7c which change over the four ports a–d of the multiplexer, each channel can input the signal every 100 msec. In this example, the above AD converters 7c–7e are used for signal inputs from various sensors $S_1$–$S_9$ for measuring the sample flow amount, temperature of detector, voltages of various parts, etc.

In other words, the contents of the AD converter changeover table shown in the above Table 2 are different respectively in coordination with the connection conditions between the gas analyzers 8–10 and the input ports of the AD converters 7a–7e as shown in FIG. 1. Since the relations of coordination between the contents of the above table 2 and the connection conditions of the gas analyzers 8–10 are combined extremely concisely, they are easy to understand. As the information provided is the minimum necessary in writing the contents in the ROMs 11–13, the capacity can be curtailed, and the generation of errors can be suppressed to the greatest possible extent.

Table 3 to be shown next is the channel information table containing the information on the analog signal of each channel to be read in as above. Accordingly, the CPU 2a controls the AD converters 7a–7e or processes the signals inputted from various channels, based on the table 3.

TABLE 3

| CH | ADC gain | spark noise | gain correction | interval for measurement |
|----|----------|-------------|-----------------|--------------------------|
| 1  | 0 | 0 | 0 | 1 |
| 2  | 0 | 0 | 0 | 1 |
| 3  | 0 | 0 | 0 | 2 |
| 4  | 0 | 0 | 0 | 2 |
| 5  | 0 | 0 | 0 | 3 |
| 6  | 0 | 0 | 0 | 3 |
| 7  | 0 | 0 | 0 | 3 |
| 8  | 0 | 0 | 0 | 3 |
| 9  | 0 | 0 | 0 | 3 |
| 10 | 0 | 0 | 0 | 3 |
| 11 | 0 | 0 | 0 | 3 |
| 12 | — | — | — | — |

In the other words, the above channel information table stores the amplitude of the amplifiers for gain adjustments (in the table, described as "ADC gain") in the AD converters 7a–7e to the analog input signals in the respective channels, flag information which shows whether is necessary to make correction to spike noise on the CPU 2a side or not, flag information which shows whether it is necessary to make gain correction or not, and interval for measurement.

In this example, because in the above ADC gain all the channels are 0, the amplitudes of the amplifiers for gain adjustment in the AD converters 7a–7e are all ×1. However, depending on the kind of the gas analyzer unit 8, the gain amounts may be 2, 3, 4, . . . , and the amplitudes of the above amplifiers may be ×2, ×4, ×8, . . . . Further, as the amounts of the spark noise and gain correction are zero in all channels, the CPU 2a does not contain any spark noise in the channels, so that it is possible to know that no noise removal is necessary or no gain correction is required.

In case the gas analyzer is a CLD, there may be produced the signal for which the above spike noise is required to be removed, or, in the case of a FID or a CLD, it may become further necessary to make a gain correction. In such a case, the requirement can be met simply by making the flag of the channel in which those signals are inputted equal to 1.

With respect to the interval for measurements, the fact that channels 1, 2 are 1 indicates that the sampling can be made at a high speed (in this example, every 25 ms). Also, the fact that channels 3, 4 are 2 shows that the sampling can be made at a medium speed (in this example, every 50 ms), and that channels 5–11 are 3 denotes that the sampling can be made at a low speed (in this example, every 100 ms).

The tables shown in the above tables 2, 3 are all those in which the information inherent to the hardware is memorized in table form according to the certain rule, irrespective of the use for the analyzer. Accordingly, as the CPU 2a can appropriately input and process each signal according to these tables irrespective of for what purpose the analyzers 3–5 are to be used, notwithstanding the single program, it is possible to make pertinent control of the respective gas analyzer units 8–10 of various kinds of analyzers 3–5. The above EEPROMs 11–13 may be memorized with the ID numbers assigned to the respective analyzers 3–5, in addition to the above AD converter changeover table and channel information table, so as to allow the CPU 2a to recognize the kind of the analyzer.

According to the present invention, various kinds of analyzers can be regarded as being identical by changing the connection condition table comprising the AD converter changeover table, channel information table, etc. in coordination with the characteristics of the gas analyzer unit. Accordingly, the labor can be reduced to the greatest possible extent at the time of the upgrade or development of the new type of apparatus. Consequently, it is possible to improve the rapidity of the upgrade work and the shortening of the period required for development.

The size of the AD converter changeover table varies by the number of the AD converters to be used, number of the input ports held by each AD converter, etc. Needless to say, the AD converters may be selected to appropriate size to meet the number of the gas analyzers A in the gas analyzer unit and the number of the sensors S which are anticipated in the future.

Further, the size of the channel information table can be changed according to the estimated number of input channels and the kind of the estimated signal processing. For example, in case that there is a necessity to make correction by quadrate equation to correct the linearity of the inputted signal, there may be added a flag to select whether to make correction by quadrate equation or not. In this example, the channel information table is exemplified on assumption of the case where the above input signals are within 12 channels, but needless to say, the channel numbers may be optionally selected.

In the foregoing example, the analyzer substrate 7 for the respective analyzers 3–5 is formed in a common circuit constitution irrespective of the kind of the analyzer, and the AD converters having the same function are used to suppress the labor required for the development of new type of apparatus and upgrade to the minimum degree, but the present invention is not limited to it. For example, in the example shown in FIG. 1, the AD converters 7b, 7c, 7e which are on the analyzer substrate 7 of the analyzer 4 may be omitted, or the AD converter 7a may be made to have no multiplexer. With such arrangements, waste of the circuit can be suppressed to the smallest extent.

In the above example, there are used electrically rewritable non-volatile memories (memory elements called in general EEPROM) as the non-volatile memory units 11–13. Alternatively, instead of them there may be used EPROM, PROM, flush memory, or chip memory so as to permit easy replacement. Also, there may by used card memories for easily replacement.

Furthermore, the memory unit of the analyzer processing unit 2 is constituted by non-volatile memories in the same manner as in the memory unit mentioned above, where the program to the CPU does not extinguish even under the condition of the power supply to the gas analyzer system being cut. However, the memory unit may be constituted by the rewritable memory (e.g., DRAM, SRAM, etc.), so that the analyzer processing unit has an external memory device. With such arrangement, it becomes possible to make the program control by the memory medium to be inserted in the external memory device, and the program control may be elastically made by altering the specification of the gas analyzer unit.

As described above, according to the gas analyzer system of the present invention, the CPU in the analyzer processing unit may regard the analyzers having different gas analyzer unit specifications to be identical by referring the above connection condition table. That is to say, with the single program working on a single CPU, a plurality of analyzers can be appropriately controlled. Even when the analyzers of the gas analyzer system have great variations such as NDIR, FID, CLD, etc., control can be made with the same program, and simplification of processing can be expected.

With respect to the analyzers, the hardware information inherent to the analyzer can be controlled by forming into tables. That is to say, even in case of upgrading of the gas analyzer unit, the system can be met simply by writing the connection condition table corresponding to the new gas analyzer unit in the memory unit, or by replacing with the memory unit in which the connection condition table is written. In other words, even in case of the change of the hardware of analyzer, the change can be covered simply by the change of the connection condition table, so that it becomes unnecessary to rewrite the program for the CPU in the analyzer processing unit.

Furthermore, as there is no necessity to load CPU in the unit of the analyzer, it is possible to simplify the constitution of the analyzer substrate of each analyzer. In addition, by providing the AD converters in sufficient numbers, it is possible to design the analyzer substrate in each analyzer commonly irrespective of the kind of the gas analysis unit at all, and the labor required for the designing can be suppressed to the greatest possible degree.

In case the above connection table has an AD converter changeover table, the CPU can appropriately change over the input port of each AD converter in conformity with the connection condition to the gas analyzer, and can adjust the reading out speed of the measuring signals inputted from the gas analyzer unit.

Further, in case the above connection condition table has a channel information table, the CPU can calculate the concentration of the measured gas by appropriately processing the measuring signal of each channel inputted from the gas analyzer unit, and can optionally make control of the AD converter in tune with the analog measuring signal inputted to each channel.

The information written as the connection condition table as described above is the information of the minimum necessary extent to represent the connection condition of the hardware inherent to each analyzer, and the coordination of the connection condition table to the connection condition of the hardware is easy to understand. Accordingly, compared with the practice of organizing the programs in conformity with the hardware of the gas analyzer unit in each unit, the information amount is outstandingly small and further easy to understand. Accordingly, the misoperations in the case of the development of new kind of apparatus or upgrade can be reduced as much as possible.

What is claimed is:

1. Control apparatus for a gas analyzer system, the gas analyzer system including a plurality of gas analyzers each having a gas analyzer unit with a plurality of outputs for analyzing a respective gas, a plurality of AD converters each having a plurality of inputs respectively connected to the outputs of the gas analyzer unit according to a connection condition, said control apparatus comprising:

an internal bus connected to an output of each AD converter;

a memory unit connected to the internal bus for storing a connection condition table which includes information for the connection condition;

a CPU bus connected to the internal bus of each of the gas analyzers; and an analyzer processing unit including a CPU connected to the CPU bus, the CPU operating in accordance with a program for controlling each of the gas analyzers.

2. A gas analyzer system comprising:

a plurality of gas analyzers each including:
a gas analyzer unit for analyzing respectively specified gases and having a plurality of outputs;
a plurality of AD converters each having a plurality of inputs respectively connected to said plurality of outputs of said gas analyzer unit according to a connection condition, each of said AD converters having an output,
an internal bus connected to said output of each of said AD converter; and
a memory unit connected to said internal bus for storing a connection condition table which includes information for said connection condition;

a CPU bus connected to said internal bus of each said gas analyzer;

an analyzer processing unit including a CPU connected to said CPU bus, said CPU operating in accordance with a program for controlling each of said gas analyzers.

3. A gas analyzer system as claimed in claim 2 wherein:

each of said inputs of each of said AD converters has a port number and a channel number assigned thereto; and said connection condition table includes an AD converter changeover table;

said memory unit storing information in said AD converter changeover table in including a port number of an input of an AD converter to be read and a channel number assigned to said input to be read, in response to said CPU reading signals from each of said gas analyzers per unit time, and providing said information sequentially per unit time.

4. A gas analyzer system as claimed in claim 3 wherein said connection condition table includes a channel information table;

said channel information table including:
channel specific information indicative of said channel number;
gain for adjusting a signal input to said channel in one of said AD converters;
a spike flag indicative of spike noise;
a gain flag indicative of any gain needed to correct said outputs of said AD converters; and
a numerical value indicative of measuring space.

5. A method for controlling a gas analyzer system, said method comprising:

providing the gas analyzer system including a plurality of gas analyzers each having a gas analyzer unit with a plurality of outputs for analyzing a respective gas, a plurality of AD converters each having a plurality of inputs respectively connected to the outputs of the gas analyzer unit according to a connection condition, an internal bus connected to an output of each AD converter, and a memory unit connected to the internal bus for storing a connection condition table which includes information for the connection condition;

providing an analyzer processing unit including a CPU connected to a CPU bus such that said CPU bus is connected to the internal bus of each, of the gas analyzers;

reading with said CPU the connection condition table stored in the memory unit of the gas analyzers;

reading with said CPU a signal input to the AD converter in the gas analyzers in accordance with the connection condition table stored in the memory unit, thereby reading out the input from the gas analyzer unit which outputs respectively different signals.

6. A gas analyzer system comprising:

a plurality of gas analyzers each including:
 a gas analyzer unit for analyzing respectively specified gases and having a plurality of outputs;
 a plurality of AD converters each having a plurality of inputs respectively connected to said plurality of outputs of said gas analyzer unit according to a connection condition, each of said AD converters having an output;
 an internal bus connected to said output of each of said AD converter; and
 a memory unit connected to said internal bus for storing a connection condition table which includes information for said connection condition;

a CPU bus connected to said internal bus of each said gas analyzer; and an analyzer processing unit including a single CPU connected to said CPU bus, said single CPU operating in accordance with a program for controlling each of said gas analyzers;

wherein said single CPU directly reads said connection condition table stored in said memory unit of said gas analyzers without the aid of additional CPUs being coupled to said internal bus of each said gas analyzer.

7. A gas analyzer system as claimed in claim 6 wherein:

each of said inputs of each of said AD converters has a port number and a channel number assigned thereto; and said connection condition table includes an AD converter changeover table;

said memory unit storing information in said AD converter changeover table in including a port number of an input of an AD converter to be read and a channel number assigned to said input to be read, in response to said single CPU reading signals from each of said gas analyzers per unit time, and providing said information sequentially per unit time.

8. A gas analyzer system as claimed in claim 7 wherein said connection condition table includes a channel information table;

said channel information table including:
 channel specific information indicative of said channel number;
 gain for adjusting a signal input to said channel in one of said AD converters;
 a spike flag indicative of spike noise;
 a gain flag indicative of any gain needed to correct said outputs of said AD converters; and
 a numerical value indicative of measuring space.

9. A method for controlling a gas analyzer system, the gas analyzer system including a plurality of gas analyzers each having a gas analyzer unit with a plurality of outputs for analyzing a respective gas, a plurality of AD converters each having a plurality of inputs respectively connected to the outputs of the gas analyzer unit according to a connection condition, an internal bus connected to an output of each AD converter, and a memory unit connected to the internal bus for storing a connection condition table which includes information for the connection condition, said method comprising:

providing an analyzer processing unit including a single CPU connected to a CPU bus such that said CPU bus is connected to the internal bus of each of the gas analyzers;

directly reading with said single CPU the connection condition table stored in the memory unit of the gas analyzers without the aid of additional CPUs disposed within each of the gas analyzers;

reading with said single CPU a signal input to the AD converter in the gas analyzers in accordance with the connection condition table stored in the memory unit, thereby reading out the input from the gas analyzer unit which outputs respectively different signals.

10. Control apparatus for a gas analyzer system, the gas analyzer system including a plurality of gas analyzers each having gas analyzer units and sensors for analyzing a respective gas, a plurality of AD converters each having a plurality of inputs respectively connected to the outputs of the gas analyzer units and sensors, and an analyzer processing unit connected to the plurality of gas analyzers, the control apparatus comprising:

a CPU capable of controlling;

a CPU bus to connect the CPU, each gas analyzer, and the plurality of AD converters;

a non-volatile memory unit connected in communication with the CPU, the gas analyzers units, and the sensors through the CPU bus, the non-volatile memory unit capable of storing a connection condition table; and a control program capable of controlling the gas analyzers and sensors.

11. The apparatus of claim 10 wherein at least one of the gas analyzers is selected from the group consisting of nondispersive infrared analyzers, flame ionization detectors, or chemi-luminescent detectors.

* * * * *

UNITED STATES PATENT AND TRADEMARK OFFICE
CERTIFICATE OF CORRECTION

| | | |
|---|---|---|
| PATENT NO. | : 6,430,477 B1 | Page 1 of 1 |
| APPLICATION NO. | : 09/107705 | |
| DATED | : August 6, 2002 | |
| INVENTOR(S) | : Asami et al. | |

It is certified that error appears in the above-identified patent and that said Letters Patent is hereby corrected as shown below:

Column 1, line 39, delete the reference numbers "30=32" and insert therefor --30-32--.

Column 12, line 39, claim 1, delete the phrase "capable of controlling" and insert therefor --to control each gas analyzer--.

Column 12, line 42, delete the word "connected".

Signed and Sealed this

Fifteenth Day of May, 2007

JON W. DUDAS
*Director of the United States Patent and Trademark Office*